United States Patent [19]

Horrobin et al.

[11] Patent Number: 5,116,871
[45] Date of Patent: May 26, 1992

[54] FATTY ACID THERAPY AND COMPOSITIONS FOR THE TREATMENT OF MYALGIC ENCEPHALOMYELITIS

[75] Inventors: David F. Horrobin; John C. M. Stewart, both of Guildford, England

[73] Assignee: Efamol Holdings PLC, Surrey, United Kingdom

[21] Appl. No.: 397,789

[22] Filed: Aug. 24, 1989

[30] Foreign Application Priority Data

Sep. 13, 1988 [GB] United Kingdom ............... 8821466
Aug. 10, 1989 [JP] Japan ........................... 8918293

[51] Int. Cl.$^5$ .................. A61K 31/20; A61K 35/78
[52] U.S. Cl. .................... 514/560; 514/558; 514/783; 424/195.1
[58] Field of Search ............. 424/195.1; 514/783, 514/560, 558

[56] References Cited

U.S. PATENT DOCUMENTS 4,388,324  6/1983  Horrobin ............... 424/312
4,513,008  4/1985  Revici et al. .
4,535,093  8/1985  Horrobin ............... 514/560
4,910,224  3/1990  Habib .................. 514/558

FOREIGN PATENT DOCUMENTS

46326/85  7/1985  Australia .
0115419   8/1984  European Pat. Off. .
2148713A  6/1985  United Kingdom .

OTHER PUBLICATIONS

Lipids vol. 23, No. 10, Oct. 1988, pp. 981-988 Williams et al Serum fatty acid proportions are altered . . . Epstein–Barr virus infection.
Annals of Internal Medicine vol. 106, No. 4, Apr. 1987, pp. 497-503 Am College Physicians, Kremer et al. Fish-oil fatty acid . . . in arthritis.
Merck Manual of Diagnosis and Therapy 15th edition R. Berkow M. D. Editor 1987 pp. 46-49 "Antiviral Drugs".
Grasmus, Udo Fats and Oils, 1986 Vancouver Can. pp. 250-254.
The Merck Index 11th Ed. 1989 Merck & Co., Rahway, NJ #3495.

Primary Examiner—Ronald W. Griffin
Assistant Examiner—Ralph Gitomer
Attorney, Agent, or Firm—Nixon & Vanderhye

[57] ABSTRACT

The use of one or more of the 6-desaturated or higher EFAs of each of the n-6 and n-3 series for the manufacture of a medicament for use in the treatment of post-viral fatigue syndrome (otherwise known as myalgic encephalomyelitis (ME)).

5 Claims, No Drawings

FATTY ACID THERAPY AND COMPOSITIONS FOR THE TREATMENT OF MYALGIC ENCEPHALOMYELITIS

FIELD OF THE INVENTION

The invention relates to fatty acid therapy and compositions.

BACKGROUND

Myalgic encephalomyelitis (ME), also known as benign ME, Royal Free disease, Icelandic disease, epidemic neurasthenia, post-viral syndrome, post-viral fatigue syndrome and by various other names, is a common illness for which there is no known treatment. The characteristic feature of the disease is that a previously healthy person, often a young or middle-aged adult, develops a syndrome characterised by severe fatigue, muscle aching, loss of concentration, headache and palpitations, the last probably indicating an abnormality of cardiac rhythm. The syndrome persists for months or years. The cause is unknown, but a careful history often reveals the occurrence of a febrile viral infection prior to the onset of the syndrome. The majority of patients have some evidence of impaired immune function and of chronic viral infections. Coxsackle and Epstein-Barr viruses are commonly involved but no single specific viral type has been implicated. It seems probable that a variety of viruses can initiate the syndrome in individuals who have an impaired immune response which predisposes to chronic infections.

GENERAL DISCUSSION

There are two main essential fatty acids (EFAs) found in the diet, linoleic acid (LA) of the n-6 series and alpha-linolenic acid (ALA) of the n-3 series. In order to be fully utilised by the body, and in order to perform all their essential functions, both LA and ALA must be 6-desaturated, to gamma-linolenic acid (GLA) in the case of LA and to stearidonic acid (SA) in the case of LA. GLA and SA are then further metabolised along the pathways shown. The 6-desaturated metabolites have many different functions within the body, particularly as components of the phospholipid structure of all cell membranes, and also as precursors to a variety of highly active regulating substances, including prostaglandins, leukotrienes and hydroxy fatty acids.

The pathways of metabolism of the n-6 essential fatty acids and the related n-3 acids sharing, it is believed, common enzymes in the two pathways, are:

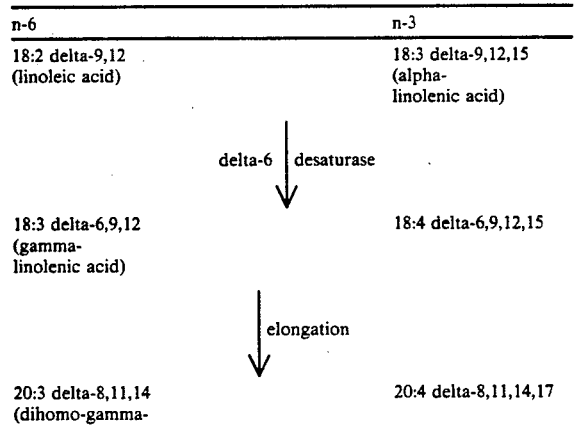

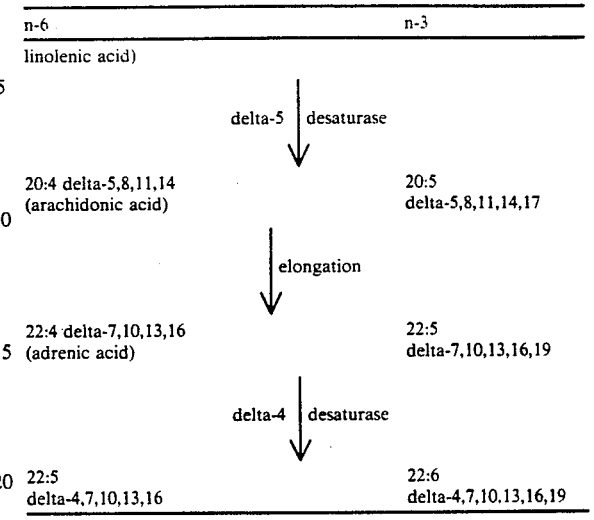

The pathways are not normally reversible nor, in man, are n-3 and n-6 series acids inter-convertible.

The acids, which naturally are of the all-cis configuration, are systematically named as derivatives of the corresponding octadecanoic, eicosanoic or docosanoic acids, e.g. delta-9,12-octadecadienoic acid or delta-4,7,10,13,16,19 docosahexaenoic acid, but numerical designation such as, correspondingly, 18:2 n-6 or 22:6 n-3 is convenient. Initials, for example, DHA for 22:6 n-3 (docosahexaenoic acid), are also used but do not serve when n-3 and n-6 acids of the same chain length and degree of unsaturation exist. Trivial names in more or less common use in the n-6 series are as shown. Of the n-3 series only 18:3 n-3 has a commonly used trivial name, alpha-linolenic acid. It was characterised earlier than gamma-linolenic acid and reference in the literature simply to linolenic acid, especially in the earlier literature, is to the alpha-acid.

There is evidence that viral infection of cells in culture can impair the ability of those cells to carry out 6-desaturation. As a result there is a defect in the manufacture within the cells of the 6-desaturated fatty acids derived from LA and ALA. There is also evidence that polyunsaturated fatty acids and their derivatives can directly inactivate certain viruses (e.g. J. D. Sands, et al, "Anti-microbial Agents and Chemotherapy 15": pages 67 to 73, 1979). It is therefore possible that cells which cannot 6-desaturate in a normal way have an impaired ability to combat virus infections initially. Impairment of 6-desaturation means that virally infected cells cannot function normally because of a reduced flow of 6-desaturated EFAs for many different purposes, and for example it has been shown that after Epstein-Barr virus infection, EFA abnormalities are correlated with persisting clinical illness.

EXPERIMENTAL WORK

Seventy patients suffering from ME were considered suitable and of these thirty six women and twenty seven men gave their consent to a randomised, double-blind, placebo-controlled trial of a mixture of 80% evening primrose oil (EPO) and 20% fish oil (herein EFAMOL MARINE (Trade Mark). 500 mg capsules were used, each containing a final amount of 7.2% (35 mg) GLA, 3.6% (17 mg) eicosapentaenoic acid (EPA) and 1.8% (11 mg) docosahexaenoic acid (DHA) along with 255 mg linoleic acid. Placebos contained olive oil, made up primarily of oleic acid with a small amount of LA (50 mg per capsule) and no 6-desaturated or higher EFAs. Patients were randomised to receive active or placebo treatment for a period of 15 weeks. At baseline and at 5, 10 and 15 weeks patients were asked to score severity of palpitations, headache and muscle ache. At the end of the trial they were asked to rate their condition in relation to that at the start of the trial as much better, better, unchanged or worse. The results are shown in the accompanying FIG. 1 and the Table below. The results were very clear-cut: 84% of the active group were better or much better and 16% unchanged, with none worse. In the placebo group 22% were better or much better, 70% were unchanged and 8% were worse. The difference between the two outcomes was very highly statistically significant ($p<0.0001$).

TABLE

Patients' assessments at the end of the trial as to whether they were much better, better, unchanged or worse as compared to the starting point. The assessments were made on a blind basis and the patients were unaware as to which treatment they had been using.

|  | ACTIVE | PLACEBO |
|---|---|---|
| Much better | 32% | 9% |
| Better | 52% | 13% |
| Unchanged | 16% | 70% |
| Worse | 0% | 8% |

This study, on clinical criteria unaffected by uncertainties on the root cause of the condition, demonstrates that administration of 6-desaturated or higher EFAs is highly effective in relieving the subjective symptoms of ME, a condition which has hitherto been regarded as untreatable. Either n-6 EFAs alone or n-3 EFAs alone have effect, but optimal results are achieved by the administration of both types of EFA.

Besides the clinical work extensive measurements of fatty acid levels in red cell membrane phospholipids were taken (FIG. 2) showing the objective effect of the medication.

Interferons and EFAs

Interferons (alpha, beta and gamma) are endogenous cytokines, first discovered because of their anti-viral actions. Interferons similar to or identical to the natural endogenous compounds can now be prepared by biotechnological methods.

Interferons act in part by enhancing the conversion of the n-6 essential fatty acid arachidonic acid (AA) to prostaglandins. If this action cannot take place, then interferons lose much or all of their anti-viral actions.

As the work above shows, we have now found that in patients suffering from fatigue after viral infections, as compared to normal individuals, there are reduced levels of both the n-6 EFAs and the n-3 EFAs. We have also found that administration of the n-6 EFAs, GLA and DGLA, together with n-3 EFAs, EPA and DHA, produces a dramatic improvement in clinical symptoms in patients with post-viral syndrome as compared to those given placebo.

Accordingly, both n-3 and n-6 EFAs must be considered involved in enhancing the body's response to viral infections and in enabling interferons to function more effectively. The co-administration of one or more interferons with one or more n-6 EFAs chosen from GLA, DGLA and AA, and/or one or more n-3 EFAs chosen from stearidonic acid, EPA, docosapentaenoic acid and DHA will greatly enhance the therapeutic efficacy of interferon.

THE INVENTION

We propose the administration of 6-desaturated EFAs or the higher acids derived from them, of the n-6 series and the n-3 series together, leading to an improvement in patients with the post-viral syndrome. It will tend to normalise EFA status of the body and may in addition have a direct anti-viral effect. Further, interferons may be used in conjunction with such administration.

More particularly, the invention lies in:

1. A new method of treatment for ME comprising administration of one or more of the 6-desaturated and higher EFAs of the n-6 series, and one or more of the 6-desaturated and higher EFAs of the n-3 series, optionally with one or more interferons also.

2. A composition for treating ME, as above.

3. A method of preparing a pharmaceutical composition for treating ME, as above.

DOSE RANGES

Each EFA may be given in a dose range of 1 mg to 100 g per day, preferably 50 mg to 20 g per day and especially preferably 500 mg to 5 g per day. Interferons, alpha, beta or gamma, are desirably in doses ranging from 500,000 to 500 million units per week (preferably 2 to 50 million and more preferably 5 to 25 million units per week) in divided, daily or 2 to 5 times weekly doses.

DERIVATIVES

The acids may be used as such or as pharmaceutically acceptable and physiologically equivalent derivatives as, for example, detailed later herein for GLA and DGLA, and reference to any of the acids is to be taken as including reference to the acids when in the form of such derivatives. Equivalence is demonstrated by entry into the pathway quoted herein, as evidenced by effects corresponding to those of the acids themselves or their natural glyceride esters. Thus, indirect identification of useful derivatives is by their having the valuable effect in the body of the acid itself, but conversion can be shown directly by gas chromatographic analysis of concentrations in blood, body fat, or other tissue by standard techniques, for example those of Pelick et al, page 23, "Analysis of Lipids and Lipoproteins" Ed Perkins, American Oil Chemists Society, Champaign, Ill., U.S.A.

In outline the method is suitably that plasma samples (1 ml) are extracted with chloroform:methanol (2:1). The extract is filtered through sodium sulphate, evaporated to dryness, and taken up in 0.5 ml chloroform:methanol. The lipid fractions are separated by thin layer chromatography or silica gel plates. The phospholipid fraction, taken to reflect essential fatty acid contents most sensitively, is methylated using boron trifluoride-methanol. The resulting methyl esters of the fatty acids are separated and measured using a Hewlett-Packard 5880 gas chromatograph with a six foot column packed with 10% silar on chromosorb WAW 106/230. The carrier gas is helium (30 ml/min). Oven temperature is programmed to rise from 165° C. to 190° C. at 2° C./min. Detector temperature is 220° C. and injector temperature 200° C. Retention times and peak areas are automatically computed by Hewlett-Packard Level 4 integrator. Peaks are identified by comparison with standard fatty acid methyl esters.

PACKS

If it is not desired to have compositions comprising different active materials together, packs may be prepared comprising the materials presented for separate, or part joint and part separate administration in the appropriate relative amounts, and use of such packs is within the purview of this invention.

DIETARY COMPOSITIONS

The invention is chiefly described in terms of methods of treatment and pharmaceutical compositions, but it will be understood that the gamma-linolenic and other acids, being in the nature of dietary supplements, can be incorporated in a dietary margarine or other foodstuffs and such are to be understood as within the term pharmaceutical composition when for the purposes set out.

FORMS AND SOURCES OF GAMMA-LINOLENIC AND OTHER ACIDS

Convenient physiologically equivalent derivatives of gamma-linolenic acid and dihomo-gamma-linolenic acid for use according to the invention as with the other acids, include salts, amides, esters including glyceride esters and alkyl (e.g. $C_1$ to $C_4$) esters, and phospholipids.

If desired, pharmaceutical compositions may be produced for use in the invention by associating the natural or synthetic acids, as such or as derivatives, with an acceptable pharmaceutical vehicle. It is, however, at present convenient to provide at least the gamma-linolenic acid in the form of an available oil having a high gamma-linolenic acid content, hence reference to "oil" herein.

At the present time known natural sources of oils having a high gamma-linolenic acid content are few and there are no commercial sources of dihomo-gamma-linolenic acid, though a fungus Mortierella alpina (Shimizu et al, JAOCS 66 No. 2, pp 237 to 241) does provide a source. One source of oils currently available is the seed of Evening Primrose species such as *Oenothera biennis L.* and *Oenothera Lamarckiana,* the oil extract therefrom containing gamma-linolenic acid (about 8%) and linoleic acid (about 72%) in the form of their glycerides, together with other glycerides (percentages based on total fatty acids). Other sources of gamma-linolenic acids are Borage species such as *Borago officinalis* which, though current yield per acre is low, provide a richer source of gamma-linolenic acid than Oenothera oil. Recent studies on fungi which can be cultivated by fermentation promise a fungal oil source.

The oil is extracted from the seed by one of the conventional methods of extraction such as cold pressure, screw pressure after partially cooking the seed, or solvent extraction.

Fractionation of a typical sample of this oil in the form of methyl esters shows the relative proportions:

| | |
|---|---|
| Palmitate | 6.15 |
| Stearate | 1.6 |
| Oleate | 10.15 |
| Linoleate | 72.6 |
| Gamma-linolenate | 8.9 |

The seed oil extracts referred to above can be used as such or can, for example, if desired, be fractionated to yield an oily composition containing the tri-glycerides of gamma-linolenic and linoleic acids as the main fatty acid components, the gamma-linolenic acid content being, if desired, a major proportion. Seed oil extracts appear to have a stabilising effect upon dihomo-gamma-linolenic acid if present.

SOURCES OF OTHER ACIDS

Natural sources of 22:4 and 22:5 n-6 acids include adrenal glands (22:5) and kidneys (22:4) obtained from slaughter houses, and 22:4 in the fat of the American Snapping Turtle. The n-3 acids are available from fish oils, particularly 20:5 n-3 and 22:6 n-3.

The acids can be isolated from these sources by, for example, saponification under mild non-oxidising conditions followed by preparative gas liquid chromatography. Synthesis of the acids is difficult but not impossible and provides another source.

PHARMACEUTICAL PRESENTATION

The compositions are conveniently in a form suitable for oral, rectal or parenteral administration in a suitable pharmaceutical vehicle, as discussed in detail, for example, in Williams British Patent Specification No. 1,082,624, to which reference may be made, and in any case very well known generally for any particular kind of preparation. Thus, for example, tablets, capsules, ingestible liquid or powder preparations can be prepared as required, and topical preparations also when the gamma-linolenic acid or other acids are absorbed through the skin. Injectable solutions of hydrolysed Oenothera oil may be prepared using albumin to solubilise the free acid.

Advantageously, a preservative is incorporated into the preparation. Alpha-tocopherol in concentration of about 0.1% by weight has been found suitable for the purpose.

It will be understood that the absolute quantity of active materials present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

EXAMPLES

ME is treated as follows:

1. Soft gelatin capsules containing 400 mg EPO and 100 mg fish oil. Four capsules twice per day.
2. Soft gelatin capsules containing 350 mg borage oil and 150 mg tuna oil. Three capsules twice per day.
3. Soft gelatin capsules containing 500 mg of 80% blackcurrant pip oil and 20% herring oil. Four capsules twice per day.
4. Soft gelatin capsules containing 500 mg of 80% fungal oil containing 20% GLA, and 20% Australian fish oil containing 17% DHA, 4% EPA and 3% arachidonic acid. Four capsules twice per day.
5. Purified GLA, in the free acid, ethyl or other ester, amide, tri-, di-or mono-glyceride, phospholipid or any other physiologically acceptable form, 250 mg, and EPA in any acceptable form, 250 mg (both calculated as the free acid). Two capsules twice per day.
6. Combinations of any 6-desaturated or higher n-6 EFA (350 mg) with any 6-desaturated or higher n-3 EFA (150 mg). One capsule twice per day.
7. Administration of 3 million units of alpha-interferon per day as a parenteral preparation with oral administration of hard gel capsules containing 280 mg GLA and 100 mg EPA at the rate of six per day.
8. Administration intravenously of a solution containing 3 million units of interferons per 500 ml, together with 2 g of lithium-GLA and 1 g of sodium-EPA.

We claim:

1. A method of treating myalgic encephalomyelitis comprising administering to a person suffering therefrom an effective amount of a mixture of a 6-desaturated essential fatty acid of the n-6 series and a 6-desaturated essential fatty acid of the n-3 series.

2. The method of claim 1 including also administering an effective amount of alpha, beta or gamma interferon in addition to said fatty acids.

3. The method of claim 1 wherein each of said n-6 and n-3 series of essential fatty acids is administered in an amount of 50 mg to 20 g per day.

4. The method of claim 3, wherein each of said essential fatty acids is administered in an amount of 500 mg to 5 g per day.

5. The method of claim 2, wherein from 5 to 25 million units of interferon are administered per week.

* * * * *